(12) United States Patent
Bydlon et al.

(10) Patent No.: US 8,007,853 B2
(45) Date of Patent: Aug. 30, 2011

(54) VITAMIN/MINERAL COMPOSITION WITH DHA

(75) Inventors: Roland J. Bydlon, Indianapolis, IN (US); William R. Hurd, Noblesville, IN (US); Prasad Nidamarty, Miamisburg, OH (US)

(73) Assignee: Xanodyne Pharmaceuticals, Inc., Newport, KY (US)

( * ) Notice: Subject to any disclaimer, the term of this patent is extended or adjusted under 35 U.S.C. 154(b) by 0 days.

(21) Appl. No.: 12/764,665

(22) Filed: Apr. 21, 2010

(65) Prior Publication Data

US 2010/0203160 A1 Aug. 12, 2010

Related U.S. Application Data

(62) Division of application No. 10/242,651, filed on Sep. 12, 2002, now Pat. No. 7,704,542.

(60) Provisional application No. 60/318,857, filed on Sep. 12, 2001.

(51) Int. Cl.
- *A23L 1/30* (2006.01)
- *A61K 35/60* (2006.01)
- *A61K 31/295* (2006.01)
- *A01N 37/02* (2006.01)

(52) U.S. Cl. ........ 426/648; 424/523; 514/502; 514/560; 514/904

(58) Field of Classification Search .................. 424/523; 514/560, 426.72, 426.73, 426.74, 904
See application file for complete search history.

(56) References Cited

U.S. PATENT DOCUMENTS

| | | | |
|---|---|---|---|
| 4,725,427 A | 2/1988 | Ashmead et al. |
| 4,752,479 A | 6/1988 | Briggs et al. |
| 4,822,816 A | 4/1989 | Markham |
| 5,070,085 A | 12/1991 | Markham |
| 5,374,657 A | 12/1994 | Kyle |
| 5,550,156 A | 8/1996 | Kyle |
| 5,670,344 A | 9/1997 | Mehansho et al. |
| 5,869,084 A | 2/1999 | Paradissis et al. |
| 5,994,404 A | 11/1999 | Coupland |
| 6,036,992 A | 3/2000 | Borror et al. |
| 6,048,846 A | 4/2000 | Cochran |
| 6,130,244 A | 10/2000 | DeMichele et al. |
| 6,197,329 B1 | 3/2001 | Hermelin et al. |
| 6,200,601 B1 | 3/2001 | Gorenbein et al. |
| 6,235,331 B1 | 5/2001 | Kataoka et al. |
| 6,258,846 B1 | 7/2001 | Hermelin et al. |
| 6,284,268 B1 | 9/2001 | Mishra et al. |
| 6,368,621 B1 | 4/2002 | Engel et al. |
| 6,479,545 B1 | 11/2002 | Levinson et al. |
| 6,488,956 B1 | 12/2002 | Paradissis et al. |
| 6,569,445 B2 | 5/2003 | Manning et al. |
| 6,569,857 B1 | 5/2003 | Hermelin et al. |
| 6,576,253 B2 | 6/2003 | Manning et al. |
| 6,576,666 B2 | 6/2003 | Hermelin et al. |
| 2001/0047036 A1 | 11/2001 | Vanderhoof et al. |
| 2002/0032234 A1 | 3/2002 | Hermelin et al. |
| 2002/0044961 A1 | 4/2002 | Kirschner et al. |
| 2002/0136809 A1 | 9/2002 | Shin et al. |
| 2002/0137749 A1 | 9/2002 | Levinson et al. |
| 2002/0173510 A1 | 11/2002 | Levinson et al. |
| 2003/0013692 A1 | 1/2003 | Gullans et al. |
| 2003/0165596 A1 | 9/2003 | Lystrup et al. |
| 2003/0211221 A1 | 11/2003 | Abril et al. |
| 2003/0216351 A1 | 11/2003 | Hermelin et al. |
| 2004/0101554 A1 | 5/2004 | Kirschner et al. |
| 2005/0037065 A1 | 2/2005 | Kirschner et al. |
| 2005/0101670 A1 | 5/2005 | Hermelin et al. |
| 2005/0106266 A1 | 5/2005 | Levinson et al. |

FOREIGN PATENT DOCUMENTS

| | | |
|---|---|---|
| EP | 0705539 A2 | 4/1996 |
| JP | 06151727 A | 5/1994 |
| JP | 07246679 A | 9/1995 |
| JP | 11244902 A | 9/1999 |

OTHER PUBLICATIONS

Neuro-DHA, http://www.Icpsolution.com/neurodha_adhd.html, copyright 2000.
Attention! Softgels, http://Icpsolution.com/attentiongels.html, copyright 2000.
How much DNA is enough?, http://www.Icpsolution.com/products.html, copyright 2000.

*Primary Examiner* — Sreeni Padmanabhan
*Assistant Examiner* — Uma Ramachandran
(74) *Attorney, Agent, or Firm* — Wood, Herron & Evans, LLP

(57) ABSTRACT

Compositions containing the fatty acid docosahexaenoic acid (DHA) in combination with at least one vitamin and mineral are provided to supplement nutrition in a mammalian diet. DHA is present in the composition in concentrated amounts, advantageously in a carrier such as marinol oil, to allow for quantities of DHA sufficient to supply expectant and new mothers and their children as recommended on a daily basis. This DHA may also be used to treat a variety of disorders in children and adults. The compositions advantageously include vitamins, minerals, and optionally other nutrients to provide a nutritional supplement which may be convenient to swallow and taken once a day.

6 Claims, No Drawings

VITAMIN/MINERAL COMPOSITION WITH DHA

CROSS REFERENCE TO RELATED APPLICATIONS

This application is a Divisional of U.S. patent application Ser. No. 10/242,651 entitled "Vitamin/Mineral Composition with DHA" filed on Sep. 12, 2002 (pending), which claims the benefit of U.S. Patent Application Ser. No. 60/318,857 filed on Sep. 12, 2001, the disclosures of which are hereby incorporated by reference herein.

FIELD OF THE INVENTION

The present invention relates generally to vitamin and mineral compositions and specifically to such compositions containing docosahexaenoic acid (hereinafter referred to as 'DHA'), for use as a dietary supplement.

BACKGROUND OF THE INVENTION

Compositions and supplements including various nutritional components, such as vitamins, minerals, and specifically DHA, are not only useful for their general nutritional qualities to supplement a diet, but also for physiological development. Such supplements are generally useful for all children and adults, and are particularly useful for a developing fetus, newborn infants, and their mothers.

In the development of a child, during both the prenatal pregnancy period and postnatal period after the child has been born, compositions consumed by the mother are generally passed to the child. For example, compositions such as vitamin/mineral supplements taken by the mother during pregnancy will elevate the level of desirable vitamins and minerals in her blood, which supplies the placenta and umbilical cord thereby passing those vitamins and minerals to the growing baby. After birth, the newborn baby receives these vitamins and minerals through nursing and ingesting the mother's breast milk during lactation.

Various different vitamins, minerals, and other nutritional elements have been found to be desirable for the perinatal development of a child. For example, vitamins such as A, folic acid, $B_1$, $B_2$, niacinamide, $B_6$, $B_{12}$, C, D, E and K, and minerals such as calcium, copper, iron, zinc, and magnesium, are all considered to be desirable and even essential for pregnant/lactating women. In addition to the desirable transfer of such vitamins, minerals, and nutritional elements to the developing child, the compositions are also desirable for replenishing the vitamin, mineral and/or other nutritional deficiencies in the mother's body.

One such nutritional element that is desirable for perinatal child development is docosahexaenoic acid (DHA), a member of the omega-3 family of fatty acids. DHA has been found to be essential for the healthy development of the cerebral cortex of the brain and retina in a baby as well as in an adult. It has been estimated that about half of the quantity of DHA in a fetus' body accumulates in the brain before birth and about half after birth, an indication of the importance of DHA to the fetus during pregnancy and then to the young infant during lactation. The baby generally receives DHA through the placenta during pregnancy, and in breast milk after birth and during lactation. To that end, a mother taking supplements containing DHA during both pregnancy and after childbirth will elevate the DHA levels in her blood thereby supplying the baby. Thus, with regular DHA dosages, the baby will receive adequate levels of DHA for healthy neurological and vision development during prenatal and postnatal periods, and the depleted levels of DHA in the mother are restored.

In addition, the nutritional and health benefits of DHA for the mother are also desirable. For example, supplementation of DHA for a mother has been shown to help in the prevention of depression, including postpartum depression, after the baby is born. Further, the benefits and positive effects of DHA extend well past infancy and into childhood as well. For example, supplementation of DHA in the nutritional regimen of a child has been found to be desirable in the prevention of attention deficit/hyperactivity disorder in children.

Still further, DHA has also been found to be important for the immunological system, cardiovascular system, central nervous system, and, in essence, DHA generally plays some role in every organ in the body. For example, immune response disorders, such as rheumatoid arthritis and inflammatory bowel disorder have been reduced by DHA supplementation in a diet. DHA has desirable effects in preventing heart disease and lowering the level of undesirable triglycerides in the blood. Furthermore, DHA supplementation has been found to be useful in preventing Alzheimer disease and dementia in elderly patients. Thus, it is desirable to provide DHA to adults as well as to children.

Research has shown that children over the age of five and adults need about 480 mg of DHA per day for the first three months of supplementation. After three months a maintenance dose of half of this amount is recommended. Children under the age of five should be given about 240 mg of DHA a day from day one.

Dietary supplements, typically in the form of a tablet or capsule, are commercially available to provide expecting mothers, new mothers, children and adults with nutritional elements including vitamins and minerals needed to supplement their diet. DHA supplements are also available. While currently-available supplements, and in particular pre-natal supplements, contain a multitude of vitamins and minerals in a single tablet or capsule, fatty acids such as DHA are not included in the tablet or capsule in recommended quantities. DHA, therefore, is provided in such quantities in a separate, independent supplement. Thus, persons, particularly mothers, both expecting and lactating, must consume more than one supplement in order to get the proper amounts of vitamins, minerals and DHA that they may need for proper development, and more specifically, for the healthy development of a fetus and/or a nursing infant. Taking multiple supplements is a particular hardship for a pregnant woman or a new mother.

For example, some commercially available supplements include DHA, with vitamins and/or minerals. However, such compositions generally contain only small, or even trace, amounts of DHA therein. One such supplement, 'Attention' capsules for children, commercially available from Icpsolution, contains only 83 mg of DHA per capsule. Thus, the child must take three capsules to get the recommended daily dosage of DHA. Furthermore, such a supplement is not directed to the needs of a pregnant or lactating mother and her child.

U.S. Pat. No. 6,258,846 discloses nutritional supplements containing 10-100 mg of DHA along with other vitamins and minerals. However, a mother would have to take more than two supplements per day to consume the recommended daily dose and/or a healthy dose. An expecting mother would have to take even more than that to properly supplement her own body as well as that of the growing fetus.

U.S. Pat. No. 6,200,601 discloses a nutritional supplement containing DHA in combination with some vitamins needed on a daily basis. However, the supplement is not directed to the needs of a pregnant or lactating mother and her child and does not include the much needed minerals and consequently, these minerals must be taken as a separate tablet or capsule on a daily basis or as necessary.

As a result, the prior art compositions and supplements do not adequately address the levels of DHA, vitamins and minerals needed by adults and/or children and particularly do not address the levels needed in the blood supply of a mother during pregnancy and desired in breast milk during lactation. As may be appreciated, prenatal and postnatal times are often very busy and sometimes stressful for a mother. This is particularly so if the child being born has older siblings also needing the mother's care and attention. As such, maintaining a nutritional regimen by taking supplements, and even only a single supplement, can often be a difficult task. It is particularly difficult, however, when multiple supplements have to be taken in order to obtain all the necessary nutritional elements, including vitamins, minerals, and other compositions, both throughout pregnancy and in the postnatal period. If the regimen becomes too overwhelming, the mother may simply neglect taking the supplements, not only depriving herself of the desirable nutrition in the supplements, but also robbing the baby of the benefits, as well.

Therefore, it is desirable to ease the burden of an expectant mother during and after pregnancy. It is particularly desirable to encourage an expectant mother to take the necessary nutritional supplements in the perinatal period which will ensure her health, as well as the health and proper development of the baby.

It is further desirable to supply DHA to a mother during the perinatal period in levels sufficient to ensure that the health benefits may be realized for both herself and her child.

The problems of having to take more than one tablet/capsule of more than one supplement to get the recommended dose of DHA and other needed vitamins and minerals exists with every person, whether child or adult. Thus, it is further desirable to provide a nutritional regimen for other persons, besides mothers and developing or newborn infants, which supplies the necessary vitamins, minerals, and DHA in recommended dosages with more convenience than supplements of the prior art.

SUMMARY OF THE INVENTION

The present invention provides compositions used generally to supplement nutrition in a diet for a multitude of purposes, such as perinatal benefits, while overcoming the drawbacks associated with dietary supplements of the prior art. To this end, and in accordance with the principles of the present invention, the composition provides desirable nutrients, such as vitamins, minerals and the fatty acid DHA, in a single dosage form. The present invention further provides methods to supplement nutrition by administering the nutrients, and particularly, vitamins, minerals, and DHA, within the single dosage form such as a pill, tablet or capsule. In one embodiment, the dosage form is a capsule, such as a soft shell gelatin capsule, that is taken once a day, rather than multiple pills taken multiple times a day.

The present composition includes at least one vitamin and at least one mineral in addition to DHA. Vitamins that have been deemed essential and required for good health and nutrition include for example, Vitamin A, Vitamin B, Vitamin C, Vitamin D, Vitamin E, niacinamide, and folic acid. However, it is beneficial to include more than one vitamin, or their pharmaceutically accepted salts, in the composition. One or more minerals such as calcium, zinc, iron, copper and magnesium, or their pharmaceutically accepted salts, are also beneficial for health and included in the present composition. The vitamins and minerals are generally included in amounts suitable to supplement an average diet and to overcome average deficiencies. Other desirable components may also be included in the composition.

Desirable levels of DHA may be provided in a manageable dosage by incorporating a carrier or a vehicle highly concentrated with DHA. The carrier may be a naturally occurring vehicle, such as marinol oil, in which DHA is present. In one embodiment, the concentration of the oil or other carrier containing DHA is in the range of around 40% to 100% DHA by weight of the carrier. As such and depending upon the amount of the carrier, a composition having a high content of DHA, such as greater than 100 mg to about 600 mg, may be provided in a manageable single dose beneficially formulated into a single tablet or encapsulated in a capsule, such as a softgel capsule, hardgel capsule, or in a film. Highly concentrated DHA carriers provide compositions that are easy to swallow and are required only once a day. DHA, or a pharmaceutically acceptable salt thereof, may also be provided synthetically, without a carrier.

By combining higher quantities of DHA with essential vitamins and minerals, the present invention improves the nutritional status of women throughout prenatal pregnancy and the postnatal after birth period, and also provides for the healthy perinatal development of the baby. Particularly, the essential nutrients address the multiple deficiencies normally found in pregnant and lactating women, thereby ensuring the perinatal nutritional care of both the mother and the baby. Further, the compositions may be taken as supplements by growing children and adults, including more senior adults, to address development and health issues, particularly those associated with the inflammatory, cardiovascular, and central nervous systems.

DETAILED DESCRIPTION OF SEVERAL EMBODIMENTS OF THE INVENTION

The present invention provides compositions including DHA, vitamins, and minerals in supplementary amounts to address the dietary shortages of essential nutrients. Generally, all mammals, such as humans including children and adults, will benefit by consuming DHA and other vitamins and minerals contained in the present compositions. More particularly, expectant and new mothers, and fetuses and nursing infants, will benefit.

Docosahexaenoic acid (DHA), one member of the omega-3 fatty acid family, is particularly important in fetal development. Specifically, DHA is critical to the healthy brain and retina development in a baby. DHA is also important to the mother not only to replenish shortages from the demands of pregnancy, but also to supply the growing and developing infant through lactation. In addition, DHA has been found to be important in treating inflammatory, cardiovascular and central nervous system disorders, for example, in children as well as in adults. The present compositions containing DHA in combination with other vitamins and minerals are, therefore, useful for inhibiting or treating a wide variety of ailments and disorders as will be discussed in more detail herein.

DHA may be obtained from various sources, including natural sources and artificial sources. Natural sources include, without limitation, oils and fats from cold-water fish, such as shellfish, tuna, salmon, mackerel, herring, trout, and swordfish, anchovy, sardines, and possibly including certain types of algae. Fish are able to convert an omega-6 fatty acid, linolenic acid, in the algae to DHA to a reasonably fruitful degree whereas humans are only able to do so to a limited degree. Artificial sources include man-made DHA produced synthetically in the laboratory or by other suitable means, typically in the form of synthetic oils, waxes and fats, for inclusion into the present composition. Further non-limiting exemplary natural sources of DHA includes seed oil such as flaxseed oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, among others.

Regardless of its source, the DHA, or a pharmaceutically acceptable salt thereof, is utilized in accordance with the principles of the invention. DHA is present in the composition in amounts greater than 100 mg. In one embodiment, the composition contains DHA in a range of greater than 100 mg to a high content of about 600 mg. In another embodiment, the composition contains DHA in a range of from about 180 mg to about 500 mg. If desired, the DHA may be included in a range of from about 200 mg to about 350 mg. Advantageously, the DHA is incorporated into the final composition via a carrier or a vehicle-type component of some kind. Examples of useful carriers are natural sources of DHA, such as oils, that are biologically acceptable to mammals. Oils in general are convenient and inexpensive. Natural oils often contain DHA in concentrated amounts to provide desirable DHA levels in the final composition. In one embodiment, a suitable carrier is fish oil, also known as marinol oil. Suitable marinol oil may be purchased commercially from Loders Crokaan, Netherlands. In another embodiment, the marinol oil contains a concentration of DHA as an ingredient in the range of about 40% to 100% by weight of the oil. Such a highly concentrated DHA carrier ensures that desirable amounts of DHA may be incorporated into the nutritional supplement in a single dosage composition (eg. one tablet or capsule per day, rather than multiple tablets/capsules per day). A more manageable dosage and regimen enhances compliance by the person taking the supplement, such as a pregnant or lactating mother. High concentrations also provide compositions which may be formulated into an easy-to-swallow and relatively small-sized tablets or capsules.

The present composition also includes at least one vitamin and at least one mineral, or pharmaceutically acceptable forms thereof, respectively. The term 'pharmaceutically acceptable' as used herein with reference to a vitamin or a mineral means not only the vitamin or mineral itself but also all biologically acceptable forms of the vitamin and mineral as well, including, for example, salt forms. Biologically acceptable refers to being safe for mammalian consumption. Vitamins and minerals, in general, are desirable for health reasons. A few examples of the many health benefits are listed with the particular vitamin or mineral below. Non-limiting exemplary vitamins include vitamin A, vitamin B complex vitamins, vitamin C, vitamin D, vitamin E, vitamin K, and folic acid. When vitamin A is present in the composition, it is advantageously present in a range of about 0.002 mg to about 15 mg, or in a range of about 1 IU to about 7500 IU wherein the conversion rate of vitamin A is about 500,000 IU per gram. More advantageously, the vitamin A will be betacarotene present in about 8-9 mg.

Non-limiting exemplary vitamin B complex vitamins include thiamine ($B_1$), riboflavin ($B_2$), niacin (niacinamide), pyridoxine ($B_6$), cyanocobalamin ($B_{12}$), biotin, pantothenic acid, folic acid, inositol or combinations thereof, for example. Vitamin $B_1$, or thiamine, is essential for growth and the prevention of beriberi. When vitamin $B_1$ is present in the composition, it is advantageously present in a range of about 0.5 mg to about 50 mg. More advantageously, the vitamin $B_1$ is a monohydrate present in a range of about 2.0-2.5 mg.

Vitamin $B_2$, or riboflavin, is known to promote growth, particularly by functioning as a flavoprotein in tissue respiration. When vitamin $B_2$ is present in the composition, it is advantageously present in a range of about 0.5 mg to about 50 mg. More advantageously, the vitamin $B_2$ is present in a range of about 4.5-5.5 mg.

Vitamin $B_6$, or pyridoxine, is believed to be helpful for fat metabolism, and also for the dehydration and desulfhydration of amino acids and for the normal metabolism of trypsin. When vitamin $B_6$ is present in the composition, it is advantageously present in a range of about 0.1 mg to about 200 mg. More advantageously, the vitamin $B_6$ is the HCl salt of pyridoxine and present in the composition in a range of about 40-45 mg.

Vitamin $B_{12}$, or one of the three active forms: cyanocobalamin, hydroxocobalmin, and nitrocobalmin, is believed to influence nucleic acid synthesis, fat metabolism, conversion of carbohydrate to fat, and metabolism of glycine, serine, methionine, and choline. When vitamin $B_{12}$ is present in the composition, it is advantageously present in a range of about 2 mcg to about 250 mcg. More advantageously, the vitamin $B_{12}$ is present as 1% SD on starch and in a range of about 1.2 to about 1.7 mg.

Niacin (nicotinic acid) or its amide form, niacinamide, is believed necessary, along with other vitamins, for the prevention and cure of pellagra in humans. In addition, it functions in protein and carbohydrate metabolism. When niacinamide is present in the composition, it is advantageously present in a range of about 1 mg to about 100 mg.

When folic acid is present in the composition, it is advantageously present in a range of about 0.1 mg to about 5 mg. More advantageously, the folic acid is present in a range of about 0.5 to about 1.5 mg.

Vitamin C is known to be essential for the prevention of scurvy in humans. It also increases resistance to infections. When vitamin C is present in the composition, it is advantageously present in a range of about 10 mg to about 1000 mg. More advantageously, the vitamin C (ascorbic acid) or the pharmaceutically acceptable salt thereof, such as calcium ascorbate, is present in about 130 to about 160 mg.

When vitamin D is present in the composition, it is advantageously present in a range of about 0.001 mg to about 0.6 mg. Suitable vitamin D's include, without limitation, vitamin $D_3$ (cholecalciferol) advantageously present in range above, or in a range of about 1 IU to about 600 IU wherein the conversion rate of vitamin $D_3$ is about 1,000,000 IU per gram.

When vitamin E is present in the composition, it is advantageously present in a range of about 1.25 mg to about 125 mg. More advantageously, the vitamin E (tocopherols) is a mixture of different tocopherols, present in the range above, or in a range of about 1 IU to about 100 IU wherein the conversion rate of vitamin E is about 800 IU per gram. In one embodiment, mixed tocopherols are present in about 45 mg in the composition.

Non-limiting exemplary minerals include calcium, zinc, iron, copper and magnesium, or their pharmaceutically accepted salts. Calcium is useful in the development of bones. When calcium is present in the composition, it is advantageously present in a range of about 20 mg to about 1000 mg. More advantageously, the calcium is present as a pharmaceutically acceptable form, including salts such as calcium carbonate for example, and present in a range of about 80 to about 110 mg.

When zinc is present in the composition, it is advantageously present in a range of about 5 mg to about 100 mg.

More advantageously, the zinc is present in a pharmaceutically acceptable form such as zinc oxide, and present in a range of about 30 to about 35 mg.

Iron is useful for the production of red blood cells, particularly necessary for the production of hemoglobin in the red blood cell. When iron is present in the composition, the total elemental iron content is advantageously in a range of about 10 mg to about 200 mg. More advantageously, the iron is present in a pharmaceutically acceptable form such as an iron-amino acid chelate, or a salt such as ferrous fumarate. Any one particular form may comprise from about 1.0% to about 99% of the total elemental iron in the composition. In one embodiment of the invention, iron is present in about 72.8 mg of ferrous fumarate (32.87% iron) and also present in about 39.9 mg of ferrochel amino acid chelate (20% iron) in the final composition.

When copper is present in the composition, it is advantageously present in a range of about 0.1 mg to about 10 mg. More advantageously, the copper is present in a pharmaceutically acceptable form or salt such as cupric oxide, and present in a range of about 2.3-3.0 mg.

When magnesium is present in the composition, it is advantageously present in a range of about 5 mg to about 400 mg. The magnesium may be present in any biologically acceptable form, such as a pharmaceutically accepted salt, for example.

The present composition may also include other desirable additives such as, without limitation, starches, sugars, fats, antioxidants, amino acids, proteins, derivatives thereof or combinations thereof. Antioxidants generally improve the stability of the final composition. Inclusion of additives which assist in formulating the final composition are also desirable.

The present composition is advantageously formulated into a convenient dosage form, such as a pill or a tablet, or enclosed in a shell or capsule. Formulation of the desired ingredients, nutrients and/or additives may be accomplished by conventional methods. Advantageously, the final composition is encapsulated in a capsule, such as a gelatin capsule, and more advantageously, a soft-shell gelatin capsule. For example, compositions including the vitamins, minerals, and DHA in desired forms and quantities, such as those listed in the embodiments of the invention disclosed in Tables 1, 2 or 3 respectively, can be made by weighing the individual ingredients, and blending them together to form a homogeneous mixture for final formulation or encapsulation.

TABLE 1

RANGES OF EXEMPLARY COMPONENTS

| DESCRIPTION | QUANTITY |
| --- | --- |
| Betacarotene | about 1 IU to about 7500 IU or about 0.002 mg to about 15 mg |
| Vitamin $D_3$ | about 1 IU to about 600 IU or about 0.001 mg to about 0.6 mg |
| Vitamin E | about 1 IU to about 100 IU or about 1.25 mg to about 100 mg |
| Vitamin C | about 10 mg to about 1000 mg |
| Folic Acid | about 0.1 mg to about 5 mg |
| Vitamin $B_1$(thiamine) | about 0.5 mg to about 50 mg |
| Vitamin $B_2$(riboflavin) | about 0.5 mg to about 50 mg |
| Niacinamide | about 1 mg to about 100 mg |
| Vitamin $B_6$(Pyridoxine) | about 0.1 mg to about 200 mg |
| Vitamin $B_{12}$(Cyanocobalamin) | about 2 mcg to about 250 mcg |
| Calcium | about 20 mg to about 1000 mg |
| Zinc | about 5 mg to about 100 mg |
| Iron | about 10 mg to about 200 mg |
| DHA | about 100 mg to about 600 mg |

TABLE 1-continued

RANGES OF EXEMPLARY COMPONENTS

| DESCRIPTION | QUANTITY |
| --- | --- |
| Cu (0) | about 0.1 mg to about 10 mg |
| Mg (9) | about 5 mg to about 400 mg |

TABLE 2

COMMERCIAL-LABEL AMOUNTS

| DESCRIPTION | QUANTITY |
| --- | --- |
| Betacarotene | about 3000 IU or about 5.0 mg |
| Vitamin $D_3$ | about 400 IU or about 0.4 mg |
| Vitamin E | about 30 IU or about 37.5 mg |
| Vitamin C | about 100 mg |
| Folic Acid | about 1 mg |
| Vitamin $B_1$(thiamine) | about 1.8 mg |
| Vitamin $B_2$(riboflavin) | about 4 mg |
| Niacinamide | about 20 mg |
| Vitamin $B_6$(Pyridoxine) | about 25 mg |
| Vitamin $B_{12}$(Cyanocobalamin) | about 12 mcg |
| Calcium | about 50 mg |
| Zinc | about 25 mg |
| Iron | about 29 mg |
| DHA | about 200 mg |
| Cu (0) | about 2 mg |

TABLE 3

PRODUCTION AMOUNTS

| DESCRIPTION | QUANTITY |
| --- | --- |
| Betacarotene 30% | about 8.4 mg |
| Vitamin $D_3$ | about 0.52 mg |
| Vitamin E | about 45 mg |
| Calcium Ascorbate(82% ascorbic acid) | about 146.3 mg |
| Folic Acid | about 1.4 mg |
| Thiamine (monohydrate) | about 2.34 mg |
| Riboflavin | about 5 mg |
| Niacinamide | about 22 mg |
| Pyridoxine HCI (82.3% pyridoxine) | about 42.5 mg |
| Cyanocobalamin (1% SD on starch) | about 1.62 mg |
| Calcium carbonate (405 calcium) | about 96.9 mg |
| Zinc oxide (80.34% zinc) | about 32.69 mg |
| Ferrous fumarate (32.87% iron) | about 72.79 mg |
| Ferrochel amino acid chelate (20% iron) | about 39.87 mg |
| Marinol oil (60% DHA) | about 366.67 mg |
| Cupric oxide (80% copper) | about 2.57 mg |
| Beeswax (yellow) | about 90 mg |
| Lecithin (unbleached) | about 17 mg |
| Soybean oil | about 16.34 mg |

Table 1 represents embodiments of the invention wherein the composition contains exemplary vitamins and minerals, without limitation, along with the DHA, in ranges, such as those disclosed.

For the purposes of compliance with federal regulations, such as regarding the stability of ingredients in the composition for example, persons of ordinary skill in the art readily understand that the particular quantities of each individual ingredient may exceed that stated on the label of the final commercialized product. Thus, amounts of nutrients stated herein may be adjusted accordingly.

Accordingly, Table 2 shows commercial-label amounts for a particular embodiment. Table 3 shows the actual amounts used for the embodiment illustrated in Table 2; however, Table 3 includes the overage required for stability of various components pursuant federal regulations. For example, vitamin $B_2$ (riboflavin) is listed in Table 2 in an amount of 4 mg, whereas with an overage requirement of 25%, it is, therefore, present in an actual amount of 5 mg, as listed in Table 3.

In one embodiment of the invention, marinol oil is advantageously used as a carrier or a component that provides the DHA in the composition. If necessary, the solid components may be combined with the marinol oil component, such as by a milling process, or by other conventional means. The resulting mixture, typically a dry powder, may be filled into gelatin shells or capsules using conventional methods and preferably, a rotary-die filling process. For example, a rotory-die filling process, or other similar process, may be used to encapsulate the ingredients, typically a blend of vitamins, minerals, DHA and other elements, into gelatin capsules or similar films. This machine uses a system of rotary dies and can successfully fill the dry powder into a soft or hard shell gelatin capsule. The finished soft or hard gelatin capsules, or tablet products, may be made into a variety of colors, shapes, and sizes.

In the event that the mixture of desired vitamins, minerals, DHA and other ingredients is not a dry solid, but either a semi-solid or a liquid, the rotory-die filling process can also encapsulate the liquid, as well as combinations of liquids and powders, into gelatin capsules. In a further aspect of the capsules, slugs or compressed tablets may be enclosed in the gelatin film.

Compositions of the present invention have many uses besides perinatal development of babies and replenishing deficiencies in their mothers. For example, and in one embodiment of the invention, the present compositions containing DHA in combination with desired vitamins and minerals, in accordance with the principles of the present invention, may be used for combating and preventing cardiovascular disorders, such as heart disease, and/or lowering the level of undesirable triglycerides in the blood. Specifically, the DHA, in concentrations and contents disclosed, may be used or specifically directed to treat persons possibly at risk for heart disease and/or high triglyceride levels. In addition, DHA has been found to make platelets in the blood less likely to stick thereby reducing the potential for clotting and lessening the chance of a heart attack.

In another embodiment, the present composition provides DHA in a desirable concentration and content, in combination with one or more vitamins and minerals, to inhibit or treat central nervous system disorders. More particularly, the DHA may be used or specifically directed to assist elderly patients in combating and preventing the development and progression of Alzheimer's disease and dementia. In yet another embodiment, the DHA, in a desirable concentration and content and in combination with one or more vitamins and minerals, may be provided in the present composition to assist in the prevention of attention deficit/hyperactivity disorder in children.

In a further embodiment, the present composition provides DHA in a desirable content and concentration in combination with one or more vitamins and minerals, for inhibiting or treating inflammatory disorders. More particularly, the present compositions may be used or specifically directed to combat and reduce the effects of rheumatoid arthritis and inflammatory bowel disorder for example.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. For example, as future applications of DHA become apparent to those skilled in the art, the present invention may be used for such purposes, and not be limited to those listed above. Therefore, the invention in its broader aspects is not limited to the specific details, methods and examples described. Accordingly, departures may be made from such details without departure from the spirit or scope of applicant's general inventive concept.

What is claimed is:

1. A method of supplementing the nutrition of a pregnant or lactating female comprising:
    administering to the pregnant or lactating female a dietary supplement consisting of:
        marinol oil consisting essentially of docosahexaenoic acid (DHA) or pharmaceutically acceptable salt thereof, the DHA present in an amount from about 100 mg to about 600 mg and in a concentration of about 40% to about 60% by weight of the marinol oil,
        about 0.002 mg to about 15 mg Vitamin A,
        about 2 mcg to about 300 mg Vitamin B,
        about 10 mg to about 1000 mg Vitamin C,
        about 0.001 mg to about 0.6 mg Vitamin D,
        about 1.25 mg to about 125 mg Vitamin E,
        about 1 mg to about 100 mg niacinamide,
        about 0.1 mg to about 5 mg folic acid,
        about 20 mg to about 1000 mg calcium,
        about 5 mg to about 100 mg zinc,
        about 10 mg to about 200 mg iron in a form selected from the combination of ferrous fumarate and iron-amino acid chelate,
        about 0.1 mg to about 10 mg copper, and
        about 5 mg to about 400 mg magnesium.

2. The method of claim 1 wherein the DHA is present in a range of from about 180 mg to about 500 mg.

3. The method of claim 1 wherein Vitamin B is selected from the group consisting of Vitamins $B_1$, $B_2$, $B_6$, $B_{12}$, and combinations thereof.

4. The method of claim 1 wherein iron is present in an amount of about 10 mg to about 32 mg.

5. The method of claim 1 further comprising formulating the dietary supplement as one of a pill, tablet, or capsule prior to administration.

6. The method of claim 1 further comprising, prior to administration, formulating the dietary supplement into a single unitary dosage form to be ingested once a day, the form being one of a tablet or a capsule.

* * * * *